United States Patent [19]

Masterson

[11] Patent Number: 5,069,904
[45] Date of Patent: Dec. 3, 1991

[54] METHOD OF USING NICOTINE IN THE TREATMENT OF CONDITIONS SUSCEPTIBLE TO SAID TREATMENT

[75] Inventor: Joseph G. Masterson, Dublin, Ireland

[73] Assignee: Elan Corporation, PLC, Athlone, Ireland

[21] Appl. No.: 461,428

[22] Filed: Jan. 5, 1990

[30] Foreign Application Priority Data

Jan. 6, 1989 [IE]  Ireland ................................. 43/89

[51] Int. Cl.$^5$ .......................... A61K 6/00; A61K 9/68; A61K 9/62; A61F 13/00
[52] U.S. Cl. ..................................... 424/401; 424/440; 424/445; 424/447; 424/448; 424/449; 424/451; 424/464; 514/356; 514/926; 514/944; 514/969
[58] Field of Search ............... 424/448, 449, 447, 445, 424/440, 451, 464, 401; 514/356, 944, 926, 969

[56] References Cited

U.S. PATENT DOCUMENTS

| | | | |
|---|---|---|---|
| 4,597,961 | 7/1986 | Etscorn | 424/48 |
| 4,680,172 | 7/1987 | Leeson | 424/449 |
| 4,765,985 | 8/1988 | Leeson | 424/28 |
| 4,781,924 | 11/1988 | Lee et al. | 424/449 |
| 4,837,027 | 6/1989 | Lee | 424/449 |
| 4,839,174 | 6/1989 | Baker et al. | 424/447 |

Primary Examiner—Thurman K. Page
Assistant Examiner—D. Gabrielle Phelan
Attorney, Agent, or Firm—Marla J. Church

[57] ABSTRACT

A method of using nicotine in the treatment of various conditions susceptible to alleviation by nicotine therapy such as disease states characterized by reduced central cholinergic function. Nicotine is administered to a subject initially having a blood supply substantially free of nicotine at a dose and for a period sufficient to allow the subject to tolerate the dose and thereafter increasing the dose of nicotine at intervals until a therapeutic dose is achieved. Smokers may also benefit from the treatment regimen.

30 Claims, No Drawings

METHOD OF USING NICOTINE IN THE TREATMENT OF CONDITIONS SUSCEPTIBLE TO SAID TREATMENT

BACKGROUND OF THE INVENTION

This invention relates to a method of using nicotine in the treatment of conditions susceptible to such treatment.

Nicotine is the major alkaloid of tobacco and is the most potent alkaloid in tobacco smoke.

Nicotine has been shown to act as a primary reinforcer in animals and many of its pharmacological effects are potentially rewarding. It induces tolerances and smokers suffer from physical, as well as, subjective effects when it is withdrawn.

Nicotine also induces changes in the number of nicotinic cholinergic receptors and this is one possible mechanism underlying tolerance. Besides its main direct action at nicotinic cholinergic receptor sites, through linkage of these sites with other neurotransmitter systems, nicotine has indirect effects on the release of most of the known neurotransmitters. Through its action on the locus coeruleus it has a widespread effect on noradrenergic activity throughout the brain. It also activates ascending dopaminergic pathways thought to be involved with the brainstem and hypothalamic reward systems. Its effect on dopaminergic activity may link in with the lower incidence of Parkinson's disease among cigarette smokers. Nicotine also stimulates cholinergic neurones in the nucleus basalis of Meynert which in turn project to all regions of the cortex. This and similar actions on nerve cells in the septum, which project to the hippocampus, may be involved in the effect of nicotine on memory processes.

DESCRIPTION OF THE PRIOR ART

Various reports indicate nicotine may be of potential value in enhancing performance in people with early Alzheimer's Disease At a satellite symposium of the second EBPS meeting held in Athens in Aug. 1988, nicotine was reported to enhance certain aspects of test performance in patients early in the course of Alzheimer's Disease. At the same meeting and as reported in Nature, Nov. 17, 1988, Vol. 336, 6196, p.207 B. Sahakian (Institute of Psychiatry, London) described the preliminary results of a laboratory study of the effects of acute subcutaneous administration of a range of low doses of nicotine. The subjects tested, in addition to controls, included seven cases of subjects early in the course of probable dementia of the Alzheimer type (DAT), as diagnosed by published criteria. The results obtained indicated inter alia significant dose-related improvements in performance in the DAT subjects in a test for rapid information processing.

U.S. Pat. No. 4,765,985 describes inter alia transdermal devices and methods stated to be effective in treating memory impairment by means of controlled release of arecoline, physostigmine, naloxone and nicotine and certain derivatives thereof. U.S. Pat. No. 4,765,985 contains no information on how nicotine is to be administered for such treatment. In particular, there is no suggestion of the use of nicotine in accordance with the present invention hereinafter described which is designed to alleviate the toxicity associated with administering nicotine to non-smoking patients.

A nicotine containing chewing gum sold under the Trade Mark NICORETTE is currently being used in smoking cessation therapy. This gum contains a cation exchange resin containing 2 or 4 mg of nicotine. The release rate of nicotine from the gum is dependent upon the duration and vigour of chewing. Because buccal absorption is pH dependent, a buffer has been incorporated into the gum in an attempt to maintain the buccal environment at constant pH. While it is intended that this buffer maintain the pH in the mouth at approximately 8.5, there is no experimental data in the literature to support this conclusion. Such pH control is of considerable importance in relation to both the extent and variability of absorption of nicotine into the bloodstream from this site of administration. Another feature of such oral nicotine administration is the susceptibility of the patient to gastrointestinal upsets. Further, the poor test qualities associated with oral nicotine administration may lead to poor compliance.

Nicotine is known to show a high degree of absorption by the percutaneous route. Devices for the percutaneous or transdermal administration of nicotine are known from U.S. Pat. Nos. 4,597,961, 4,781,924 and 4,839,174.

The Specification of U.S. patent application Ser. No. 188,226, which is assigned in common herewith, discloses preparations for the once-daily, percutaneous administration of nicotine, which preparations comprise nicotine uniformly distributed in a solid, semi-solid or mucilaginous medium which can be placed in intimate contact with the skin. The disclosure of this document is incorporated herein by reference.

The aforementioned known devices, as well as others which may be contemplated hereafter to permit percutaneous absorption of nicotine, are useful for the purposes of the present invention.

It is an object of the present invention to provide improved methods for the treatment of conditions susceptible to nicotine therapy which result in increased patient compliance and the achievement of controlled and effective therapeutic levels of nicotine in such treatment.

It is a further object of the present invention to provide improved methods for the treatment of conditions susceptible to nicotine therapy, wherein the nicotine is administered on a once-daily basis.

SUMMARY OF THE INVENTION

Accordingly, the invention provides a method of using nicotine for the treatment of a condition susceptible to nicotine therapy which comprises administering a medicament containing nicotine to a subject in need of such treatment, wherein said medicament is administered to a subject initially having a blood supply substantially free of nicotine at a dose and for a period sufficient to allow said subject to tolerate said dose without showing any adverse effects and thereafter increasing the dose of nicotine at selected intervals of time until a therapeutic dose is achieved.

DETAILED DESCRIPTION OF THE INVENTION

Preferably, the initial dose of nicotine is in the range 1–5 mg/day.

Further, preferably, when said tolerance state is reached following the period of administration of said initial dose, the dose administered is increased by amounts of at least 1–5 mg/day until said therapeutic dose is achieved.

The formulations for use in accordance with the invention are distinguishable over known nicotine formulations such as those used in methods of satisfying a nicotine habit and/or treating withdrawal symptoms associated with smoking cessation, in that they deliberately contain in the first instance sub-therapeutic doses of nicotine to induce in a patient tolerance towards the side-effects of nicotine. Once tolerance is achieved, the dose of nicotine is increased until a therapeutic effect is achieved. This is in contrast to the aforementioned formulations used inter alia in methods for satisfying a nicotine habit where the formulations used contain an amount of nicotine which matches the level of nicotine to which the individual undergoing treatment is already tolerant. Thus while the types of formulations and devices used to administer nicotine in accordance with the invention correspond to those currently used in methods involving nicotine administration, the amounts of nicotine used are designed to induce tolerance against side-effects, thereby achieving more effective use of nicotine.

Preferably, said condition susceptible to nicotine therapy is a disease state susceptible to relief by administration of nicotine.

Suitably, the disease state is one characterized by reduced central cholinergic function and/or a loss of cholinergic neurons and/or a significant reduction in nicotine receptor binding. Accordingly, the disease state may be characterized by neurodegenerative dementia. Accordingly, the invention is particularly suitable for use in the treatment of a disease state which is characterized by cognition and memory impairment, such as Alzheimer's Disease.

The invention may also be used in the treatment of ulcerative colitis and related conditions.

In accordance with the invention, nicotine is preferably formulated for oral or percutaneous administration.

In the case of oral administration, the nicotine may be formulated, for example, as capsules or tablets, including those formulated for continuous or sustained release. Oral preparations may include those described in the aforementioned U.S. Pat. No. 4,765,985.

The nicotine is also suitably formulated in the form of a gum, such as that sold under the Trade Mark NICORETTE and referred to above.

However, preferably the nicotine is formulated for percutaneous administration and most advantageously is administered in a form for once-daily usage. Such forms include preparations which contain nicotine uniformly distributed in a solid, semi-solid or mucilaginous medium which are described in the aforementioned U.S. patent application Ser. No. 188,226, now U.S. Pat. No. 4,946,853. Also, such a preparation is suitably in the form of a solid or semi-solid and has a surface area in the range 2-15 cm$^2$, especially 5 to 10 cm$^2$. The preparation also suitably has a thickness in the range 0.5 to 3 mm, especially 1 to 2 mm. The preparations described in U.S. patent application Ser. No. 188,226 may also be in the form of a cream, gel, jelly, mucilage, ointment or paste.

A solidifying or gel-forming agent used in the manufacture of a preparation in accordance with U.S. patent application Ser. No. 188,226 is suitably selected from plant extracts, vegetable oils, gums, synthetic or natural polysaccharides, polypeptides, alginates, hydrocarbons, synthetic polymers, minerals and silicon compounds or a mixture thereof. More particularly, the solidifying or gel-forming agent is a synthetic or natural polysaccharide selected from alkylcelluloses, hydroxyalkylcelluloses, cellulose ethers, cellulose esters, nitrocelluloses, dextrin, agar, carrageenan, pectin, furcellaran and starch or starch derivatives and mixtures thereof.

A preparation for percutaneous administration of nicotine in accordance with the invention preferably contains from 1 to 100 mg of nicotine depending on the stage of treatment.

A preparation for the percutaneous administration of nicotine in accordance with the invention suitably contains one or more additives selected from an antimicrobial agent, a preservative, an antioxidant, a pH-controlling agent, a plasticizer, a surfactant, a penetration enhancer, a humectant, a local anaesthetic and a rubefacient or a mixture thereof.

A preparation in accordance with U.S. patent application Ser. No. 188,226, U.S. Pat. No. 4946853 for use in accordance with the present invention may be adapted to be received in a receptacle of a device which can be held in contact with the skin. Likewise the preparation may be incorporated in a self-adhesive patch, a bandage or a plaster. The preparation may include a priming dose of nicotine in a layer of adhesive material defining the skin-contacting surface of the preparation and which layer is freely permeable to the nicotine contained in the solid, semi-solid or mucilaginous medium. Alternatively, the preparation may include a priming dose of nicotine in a peripheral layer of adhesive material defining part of the skin-contacting surface of the preparation.

As indicated above, nicotine may also be administered from a device of the type described in U.S. Pat. Nos. 4,597,961, 4,765,985, 4,781,924 or 4,839,174.

A device preparation for the percutaneous administration of nicotine in accordance with the invention may be applied to the flexor surface of the forearm, including the wrist, and also the ankle. Other suitable application sites include the upper chest and the shoulder. Generally the forearm is the preferred site of application since it shows the greatest consistency from individual to individual in terms of nicotine absorption relative to other sites for administration because of the amount of tissue at such site. Blood vessels are found close to the surface of the skin at such sites which facilitate the uptake of nicotine into the systemic circulation.

On contact of such a nicotine-containing device/preparation with the skin, the nicotine starts to migrate rapidly from the device/preparation to the humid interface at the point of contact and then through the skin and into the bloodstream. The rate and extent of this percutaneous absorption is dependent on several factors including:

a) The amount of nicotine in the device/preparation;
b) The surface area of the device/preparation; and
c) The nature of any rate-controlling membrane forming part of the device/preparation.

In the case of preparations according to U.S. patent application Ser. No. 188,226 it is the skin itself that forms the rate controlling barrier and not the dosage form comprising the preparation, the effect of nicotine loading will only be observed in terms of systemic nicotine levels below a threshold loading level. Below this threshold the amount of nicotine in the dosage form is the factor which determines the concentration gradient that in turn controls the rate of absorption. Above this threshold increasing drug loading has no effect on absorption as the ability of the skin to absorb nicotine is saturated. However, such drug loading does have the effect of prolonging the time course of drug delivery by providing a larger drug depot. In order to increase the extent of absorption above the threshold it is necessary to increase the area of absorption by increasing the surface area of the dosage form so that a larger area of the skin is in contact with the nicotine.

The invention will be further illustrated by the following Examples.

EXAMPLE 1

A range of nicotine-containing patches were prepared in accordance with the procedure of Example 1 of U.S. patent application Ser. No. 188,226, U.S. Pat. No. 4,946,853 and containing 2.5, 5, 7.5, 10, 15, 25 and 30 mg of nicotine.

EXAMPLE 2

Nicotine-containing patches are prepared in accordance with the procedure of Example 1 except that 10 wt% liquid nicotine is added to a mixture of 20 wt% Pellethane (Pellethane is a Trade Mark) 2363-80AE pellets (available commercially from Dow Chemical, Midland, Michigan, U.S.A.) in tetrahydrofuran. Patches containing the desired range of nicotine are obtained by adjusting the wt% of liquid nicotine and/or varying the surface area of the patches.

EXAMPLE 3

A nicotine transdermal system is prepared according to Example 2 of U.S. Pat. No. 4,781,924 wherein the drug reservoir comprises 42% nicotine tartrate, 18% $Na_2CO_3$ and 40% ethylene/vinylacetate copolymer of the type described in U.S. Pat. No. 4,144,317. This system has a PVA rate controlling membrane about 1.5 mils (~38 μm) thick and a silicone adhesive layer. A suitable range of nicotine doses can be delivered by varying the percentage of nicotine tartrate in the system.

In-Vivo Study

A study was carried out on a range of subjects to determine the efficacy of nicotine administration in accordance with the invention. The subjects for the study were ten elderly persons diagnosed as having senile dementia of the Alzheimer's type (SDAT). Nicotine was administered percutaneously by means of patches prepared in accordance with Example 1 applied to the flexor surface of the forearm or to the upper inner arm or shoulder according to the wishes of the persons taking part in the study.

One or two patches containing 2.5, 5, 7.5, 10, 15, 25 and 30 mg of nicotine were successively applied in accordance with the treatment regimen of the invention over the duration of the study, to permit doses in the range 2.5–60 mg/day to be administered.

Tests for rapid visual information processing, which involve assessment of working memory and attention, were carried out at the end of each stage of treatment, i.e. when the subjects had completed treatment with a given concentration of nicotine and before commencing treatment with a patch of the next higher concentration.

The results showed a considerable improvement in performance, which was dose-related, in the aforementioned test for rapid visual information processing. The improvement is particularly marked for subjects with SDAT when the dose administered is between 20 and 60 mg per day.

It will be appreciated use of nicotine in accordance with the invention allows for more controlled and efficacious treatment of persons undergoing therapy with nicotine and is less likely to lead to adverse side-effects due to overdosing.

The foregoing description of the present invention is directed to the treatment of non-smoking patients for whom administration of significant quantities of nicotine could be very toxic. However, it will be appreciated that smokers having increased tolerance to the effects of nicotine can also benefit from the present invention by the administration of nicotine in accordance with the invention. In the case of smokers, the dose being administered does not take into account any nicotine already present in the bloodstream from the use of tobacco products.

What I claim is:

1. A method of treating a condition susceptible to nicotine therapy which comprises administering a medicament containing nicotine to a subject in need of such treatment, wherein said medicament is administered to a subject initially having a blood supply substantially free of nicotine at a sub-therapeutic dose in the range of 1–5 mg/day and for a period of time sufficient to allow said subject to tolerate said dose without showing any adverse effects and thereafter increasing the dose of nicotine at selected intervals of time until a therapeutic dose is achieved.

2. The method according to claim 1, wherein when said tolerance state is reached following the period of administration of said initial dose, the dose administered is increased by amounts of at least 1–5 mg/day until said therapeutic dose is achieved.

3. The method according to claim 1, wherein said condition susceptible to nicotine therapy is a disease state susceptible to relief by administration of nicotine.

4. The method according to claim 3, wherein the disease state is characterized by reduced central cholinergic function.

5. The method according to claim 4, wherein the disease state is characterized by a loss of cholinergic neurons.

6. The method according to claim 3, wherein the disease state is characterized by a significant reduction in nicotine receptor binding.

7. The method according to claim 6, wherein the disease state is characterized by neurodegenerative dementia.

8. The method according to claim 3, wherein the disease state is characterized by cognition and memory impairment.

9. The method according to claim 8, wherein the disease is Alzheimer's disease.

10. The method according to claim 3, wherein the disease is ulcerative colitis.

11. The method according to claim 1, wherein the nicotine is formulated for oral administration.

12. The method according to claim 11, wherein the nicotine is in the form of tablets or capsules.

13. The method according to claim 11, wherein the nicotine is contained in a gum.

14. The method according to claim 1, wherein the nicotine is formulated for percutaneous administration.

15. The method according to claim 14, wherein the nicotine is administered in the form of a preparation which comprises nicotine uniformly distributed in a solid, semi-solid or mucilaginous medium which can be placed in intimate contact with the skin.

16. The method according to claim 15, wherein the preparation is in the form of a solid or semi-solid and has a surface area in the range 2 to 15 cm$^2$.

17. The method according to claim 16, wherein the preparation has a surface area in the range 5 to 10 cm$^2$.

18. The method according to claim 15, wherein the preparation has a thickness in the range 0.5 to 3 mm.

19. The method according to claim 18, wherein the preparation has a thickness in the range 1 to 2 mm.

20. The method according to claim 15, wherein the preparation is in the form of a cream, gel, jelly, mucilage, ointment or paste.

21. The method according to claim 15, wherein the solid, semi-solid or mucilaginous medium is formed by adding a given amount of nicotine to a solution of a solidifying or gel-forming agent or mixture thereof in a suitable solvent or mixture of solvents, and mixing or treating the mixture thereby obtained so as to form said solid, semi-solid or mucilaginous medium, the solidifying or gel-forming agent being selected from the group consisting of plant extracts, vegetable oils, gums, synthetic or natural polysaccharides, polypeptides, alginates, hydrocarbons, synthetic polymers, minerals and silicon compounds or a mixture thereof.

22. The method according to claim 21, wherein the solidifying or gel-forming agent is a synthetic or natural polysaccharide selected from the group consisting of alkylcelluloses, hydroxyalkylcelluloses, cellulose ethers, cellulose esters, nitrocelluloses, dextrin, agar, carrageenan, pectin, furcellaran and starch or starch derivatives or a mixture thereof.

23. The method according to claim 15, wherein the preparation contains from 1 to 100 mg of nicotine depending on the stage of treatment.

24. The method according to claim 15, wherein the preparation contains one or more additives selected from the group consisting of an antimicrobial agent, a preservative, an antioxidant, a pH-controlling agent, a plasticizer, a surfactant, a penetration enhancer, a humectant, a local anaesthetic and a rubefacient or a mixture thereof.

25. The method according to claim 15, wherein the preparation is adapted to be received in a receptacle of a device which can be held in contact with the skin.

26. The method according to claim 15, wherein the preparation is incorporated in a self-adhesive patch, a bandage or a plaster.

27. The method according to claim 1, wherein the nicotine is administered on a once-daily basis.

28. The method according to claim 27, wherein the nicotine is administered in the form of a preparation which comprises nicotine uniformly distributed in a solid, semi-solid or mucilaginous medium which can be placed in intimate contact with the skin.

29. A method of using nicotine for the treatment of a condition susceptible to nicotine therapy which comprises administering a medicament containing nicotine to a subject in need of such treatment, wherein said medicament is administered to said subject at a dose and for a period sufficient to allow said subject to tolerate said dose without showing any adverse effects and thereafter increasing the dose of nicotine at selected intervals of time until a therapeutic dose is achieved.

30. A method of treating a condition susceptible to nicotine therapy which comprises administering percutaneously a medicament containing nicotine to a subject in need of such treatment, wherein said medicament is administered to a subject initially having a blood supply substantially free of nicotine at a sub-therapeutic dose in the range of 1–5 mg/day and for a period of time sufficient to allow said subject to tolerate said dose without showing any adverse effects and thereafter increasing the dose of nicotine at selected intervals of time until a therapeutic dose is achieved.

* * * * *